United States Patent [19]
Green et al.

[11] Patent Number: 5,976,577
[45] Date of Patent: Nov. 2, 1999

[54] PROCESS FOR PREPARING FAST DISPERSING SOLID ORAL DOSAGE FORM

[75] Inventors: Richard Green, Wiltshire; Patrick Kearney, Swindon, both of United Kingdom

[73] Assignee: RP Scherer Corporation, Troy, Mich.

[21] Appl. No.: 08/891,205

[22] Filed: Jul. 11, 1997

[51] Int. Cl.$^6$ ........................................................ A61K 9/14
[52] U.S. Cl. ........................... 424/490; 424/400; 424/451; 424/455; 424/456; 424/457; 424/458; 424/459; 424/460; 424/461; 424/484; 424/485; 424/486; 424/487; 424/488; 424/489
[58] Field of Search ..................................... 424/400, 451, 424/455–1, 484–98

[56] References Cited

U.S. PATENT DOCUMENTS

| | | | |
|---|---|---|---|
| 5,330,763 | 7/1994 | Gole et al. | 424/484 |
| 5,670,490 | 9/1997 | Whistler | 514/54 |

*Primary Examiner*—Jose' G. Dees
*Assistant Examiner*—Kathryne E. Shelborne
*Attorney, Agent, or Firm*—Nixon & Vanderhye

[57] ABSTRACT

Process is provided for preparing an oral solid rapidly disintegrating freeze-dried dosage form of a pharmaceutically active substance having an unacceptable taste, wherein prior to freeze drying, a suspension of uncoated or coated coarse particles of a pharmaceutically active substance in a carrier material is cooled to reduce the viscosity and minimize release of the active substance during processing, as well as beyond the point of disintegration of the form in the mouth, to minimize bad taste from the drug.

23 Claims, No Drawings

PROCESS FOR PREPARING FAST DISPERSING SOLID ORAL DOSAGE FORM

The present invention relates to the production of rapid dispersing solid dosage forms. More particularly, the invention provides a low temperature process for preparing rapidly disintegrating solid dosage forms containing drug particles. The drug particles may be uncoated or coated with a water-insoluble polymer or lipid material which prevents release of the drug during processing, masks the taste of the drug in the mouth, and permits controlled release of the drug after swallowing.

BACKGROUND OF THE INVENTION

It is well known to provide pharmaceutically active substances for oral administration in the form of tablets, pills or capsules. The tablet, pill or capsule is generally swallowed with water so that the pharmaceutically active substance can be absorbed by the gastro-intestinal tract. For some patients, swallowing the tablet, pill or capsule is difficult or impossible; this is particularly the case for pediatric patients and geriatric patients. Similar difficulties are often encountered when trying to administer tablets to non-human animals which may be uncooperative about taking tablets, pills or capsules.

Oral solid pharmaceutical dosage forms which rapidly disintegrate in the mouth and methods for their preparation have been proposed in GB A-1548022 and GB-A-2111423. The solid dosage forms as disclosed comprise an open matrix network carrying the pharmaceutically active substance, with the open matrix comprising a water-soluble or water-dispersible carrier material which is inert towards the pharmaceutically active substance. The solid dosage forms are prepared by the sublimation or removal of solvent from a solution or suspension comprising the pharmaceutically active substance and the carrier material. Sublimation or removal of solvent is preferably carried out by freeze drying. A typical approach is to dose a drug suspension into free form blisters followed by rapidly freezing the suspension and then freeze drying. Freeze drying removes the ice to leave a porous tablet which, when placed on the tongue, disperses in a few seconds. The drug particles are then swallowed with the saliva.

Other methods for preparing oral solid pharmaceutical forms which rapidly disintegrate in the mouth are disclosed in U.S. Pat. Nos. 5,039,540; 5,120,549; and 5,330,763, as well as PCT/JP93/01631 and PCT/US93/12566. Other patents are U.S. Pat. Nos. 4,760,093; 4,760,094; and 4,767,789, and European patent application 94305535.0.

While the solid dosage forms referred to above overcome the problem of swallowing tablets, pills or capsules, the patient will taste the pharmaceutically active substrate as the dosage form disintegrates in the mouth. Many pharmaceutically active substances have a bitter or unpleasant taste making them unsuitable for incorporation into a delivery system that rapidly disperses in the mouth. Sweeteners and flavoring agents can be used to mask the unpleasant taste, but in many instances this is still not sufficient to adequately mask the unpleasant taste.

An alternative approach to masking drugs having a bitter or unpleasant taste is to coat the drug particles with a polymer, for example a water insoluble polymer. The presence of the polymer coating around the drug particle prevents the drug from dissolving in the mouth and thereby avoids the bad taste. However, during production of freeze dried dosage forms, wherein a drug suspension is dosed into free form blisters followed by rapidly freezing of the suspension and freeze drying, drug release tends to occur, which leads to the drug being immediately available when the dosage form disperses in the mouth.

One method of limiting the rate of drug release is to increase the particle size of the coated drug particles. These can be coated more effectively, and also due to a decrease in the surface area compared with smaller particles, will decrease the release rate of the drug. A consequence of the use of large particles however the rapid sedimentation during processing as a suspension, and the resultant variation in the amount of drug per unit.

U.S. Pat. No. 5,384,124 describes a system in which a thick paste is formulated prior to freeze drying to prevent sedimentation of microsphere coated drug particles. The paste also contains amounts of a suspension agent in excess of its solubility limit to help prevent sedimentation of the microspheres during lyophilization. The presence of these additional components leads to a product with a high solids content which generally does not disperse until thirty seconds or longer (sometimes up to 1 to 3 minutes) after administration.

A need exists for improved rapidly disintegrating dosage forms which overcome the disadvantages noted above. In particular, a need exists for a dosage form which does not give rise to a bad taste when taken orally but which provides controlled release of the drug upon swallowing. The present invention provides such improved rapidly disintegrating dosage forms and processes for their preparation by allowing processing of coarse coated particles without affecting the physical properties of the dried units. The invention can also be used to enable processing of coarse uncoated drug material, preventing the need to obtain size reduced material and an additional manufacturing stage.

DESCRIPTION OF THE INVENTION

It has now been found, in accordance with the present invention, that it is possible to produce fast dispersing dosage forms which disintegrate rapidly in the mouth and which do not depend on the use of sweetening or flavoring agents to mask the taste. The dosage forms have good mouth feel and do not exhibit premature release of the drug in the mouth. The invention is based on the discovery that it is possible to produce a fast dispersing freeze-dried dosage form containing drug particles which may be uncoated or coated with a polymer or lipid material which exhibit minimal release of the drug in the mouth. This is achieved by using coarse coated drug particles and controlling the viscosity of the suspension by reducing the temperature during the holding time in suspension to minimize sedimentation of the particles without altering the physical properties of the dried units. The resulting dosage form exhibits delayed release of the drug for a time at least sufficient to mask the taste in the mouth before swallowing, and typically for a longer period of time to provide controlled or sustained release of the drug after swallowing.

In accordance with one aspect, the present invention provides a rocess for preparing an oral solid rapidly disintegrating dosage form of pharmaceutically active substance, comprising forming a suspension n a continuous phase of coarse particles of the pharmaceutically active substance in a carrier material, reducing the temperature of the suspension to increase the viscosity of the suspension and minimize sedimentation of the particles, forming discrete units of the cooled suspension, and removing the continuous phase to produce the rapidly disintegrating form.

The term "coarse particles" as used herein means drug particles having a size such that coatings can be formed thereon which are sufficiently intact and continuous to prevent or minimize loss of the drug during processing to form the dosage forms or during disintegration of the dosage form in the mouth prior to swallowing. Size of the particles has an important effect on the rate of release of drug when coated. A smaller particle has a much larger overall surface area for diffusion. As a result, the rate of release of drug is greater the smaller the particle. Current coating techniques are able to effectively coat particles greater than 100 $\mu$m, whereas particles less than 100 $\mu$m may not have an intact coat, which will result in rapid release of the drug once in suspension. Coating of larger particles therefore decreases the rate of release of drug. Typically, according to the present invention, the coarse particles may have a size of up to 1 millimeter, although the average size is generally up to about 500 $\mu$m, for example 75 to 400 $\mu$m, more usually in the region of about 100–300 $\mu$m. In this size range, it is possible to apply a uniform intact coating on the particle in order to achieve efficient freeze-dried dosage forms with slow drug release rate.

Increasing the particle size gives rise to increased sedimentation rate of the particles in suspension. This causes difficulties in obtaining uniformity of dose in each dosage form and can also cause splitting of the units if the drug particle sediments in the individual blister pockets before being frozen. The present invention overcomes this problem by adjusting the viscosity by reducing the temperature of the fluid suspension by an amount such as to increase the viscosity to a level sufficient to prevent or substantially eliminate settling out of the drug particles, preferably over a period of about 5 minutes. The temperature of the suspension is generally reduced from about 23–25° C. to about 14–20° C., typically to about 15–19° C.

According to the present invention, adjustment of the temperature of the suspension can alter the viscosity of the mix without effecting the properties of the dried units. This prevents rapid sedimentation of the drug particles, which is necessary to prevent rapid release of active agent while at the same time maintaining rapid disintegration times without gummy or gritty sensation.

The carrier material which forms a network or matrix containing the pharmaceutically active substance after removal of the continuous phase may be any water-soluble or water-dispersible material that is pharmaceutically acceptable, inert to the pharmaceutically active substance and which is capable of forming a rapidly disintegrating network, i.e. disintegrates within 10 seconds or less in the mouth. The preferred carrier material for use in the present invention is gelatin, usually pharmaceutical grade gelatin. Other substances may be used as the carrier material are, for example, hydrolyzed dextrose, dextran, dextrin, maltodextrin, alginates, hydroxyethyl cellulose, sodium carboxymethyl cellulose, microcrystalline cellulose, corn-syrup solids, pectin, carrageenan, agar, chitosan, locust bean gum, xanthan gum, guar gum, acacia gum, tragacanth, conjac flower, rice flower, wheat gluten, sodium starch glycolate, soy fiber protein, potato protein, papain, horseradish peroxidase, glycine and mannitol.

It is possible to adjust the viscosity of the suspension sufficiently to prevent rapid sedimentation of drug particles up to 400 $\mu$m. The use of particles in this size range can prevent release of drug during the mixing stage. As demonstrated in the working examples, when gelatin is used, it has been found that reducing the holding temperature of the suspension from about 23° C. to about 15° C., the viscosity of the suspension is increased sufficiently to prevent any sedimentation over a five-minute period. For a placebo formulation, the viscosity at 25° would be approximately 1.5–4.0 mPa.s, which would be expected to increase to between 20–50 mPa.s at 15° C., when measured at 500 $s^{-1}$ using a Haake VT550 viscometer with an NV sensor. The viscosity of a particular formulation will vary greatly, however, depending on the drug concentration and properties. The data in Example 2 shows a viscosity at 23° C. of 36 mPa.s which increases to 73 mPa.s upon cooling to 15° C. The higher values in this example are due to the presence of an additional 19.5% drug material but a significant increase in viscosity is again observed.

The ideal properties of the dried units can be maintained by a slight alteration in the polymeric carrier material or the temperature used. By varying the polymer level, a slightly different temperature will be required to maintain unit properties of hardness and disintegration, whilst preventing sedimentation. The polymer level used must therefore be optimized with the holding temperature, as alterations in either will affect the sedimentation rate, unit hardness and disintegration time.

A further advantage realized in the use of temperature modification of the suspension is the consequent decrease in the rate of release of drug from particles which have been coated. Diffusion processes are temperature dependent. By holding the suspension at a lower temperature and at higher viscosity, the rate of release of drug from the coated particles is reduced. This allows longer available mixing times before release of drug has reached a point where the bitter or unpleasant taste is no longer masked. This is useful for the production process where dosing of large batches takes a number of hours. Drug release from the coated particles does occur gradually, but the process of the invention decreases this rate substantially allowing longer production run times.

The term "rapidly disintegrating" as used herein means that the solid dosage form will disintegrate in water at 37° C. in 60 seconds or less. The forms usually disintegrate in about 5–20 seconds, more usually 5 to 10 seconds or less, when tested by the following procedure which is analogous to the Disintegration Test for Tablets, B.P. 1973 which is described in British patent number 1548022:

Apparatus: this comprises a glass or suitable plastic tube 80 to 100 mm long, with an internal diameter of about 28 mm and an external diameter of 30 to 31 mm and fitted at the lower end, so as to form a basket, with a disk of rust-proof wire gauze complying with the requirements for a No. 1.70 sieve (B.P. 1973, page A136).

A glass cylinder is provided with a flat base and an internal diameter of about 45 mm containing water not less than 15 cm deep at a temperature between 36° and 38° C.

The basket is suspended centrally in the cylinder in such a way that it can be raised and lowered repeatedly in a uniform manner so that at the highest position the gauze just breaks the surface of the water and at the lowest position the upper rim of the basket just remains clear of the water.

Method: one shaped article is placed in the basket and raised and lowered in such a manner that the complete up and down movement is repeated at a rate equivalent to 30 times a minute. The shaped article is disintegrated when no particle remains above the gauze which would not readily pass through it.

In accordance with another aspect of the invention, there is provided an oral solid rapidly disintegrating dosage form of a pharmaceutically active substance when prepared by the process of the invention.

In yet a further aspect, the invention provides an oral solid rapidly disintegrating dosage form of a pharmaceutically active substance comprising coarse particles of the active substance having an intact coating of a polymer or lipid material homogeneously dispersed in a matrix of a water soluble or water dispersible carrier material. The optimum size of the coated particles is in the region of about 50 μm to 400 μm, preferably about 100–300 μm.

The present invention solves a number of problems associated with rapidly disintegrating dosage forms. In particular, the larger sized particles employed allows for the formation of a continuous intact coating on the drug particles which prevents or minimizes early release of the drug during processing, and also prevents early release during rapid disintegration of the dosage form in the mouth. The coating also can be such as to provide controlled or sustained release of the drug so that drug release begins at a particular time after administration or when the drug has reached a particular location within the body.

The coated particles may be produced using any of the coating techniques capable of producing particles in the size range of interest. Examples are solvent evaporation, solvent extraction, coarcevation, spray congealing, spray drying, pan coating, air suspension techniques, spheronization, lyposomes, complex formation, hot-melt encapsulation, interfacial polymerization, electrostatic encapsulation, ion-exchange resins, centrifugal processes, or combinations thereof.

The coated particles can contain up to about 98% by weight of the pharmaceutically active substance. More usually this amount is 10% to 95% by weight.

Generally, the coating on the particles is a polymer or lipid material and serves to prevent loss of the pharmaceutical agent during processing, as well as delaying release of the pharmaceutically active substance beyond the point of disintegration of the form in the mouth. Any suitable polymer or lipid or combination can be used as the coating material. Examples of suitable polymers include cellulose and derivatives such as ethylcellulose, hydroxyethylcellulose, hydroxypropylmethylcellulose, hydroxypropylcellulose, methylcellulose, cellulose acetate, cellulose acetate phthalate, hydroxypropylmethylcellulosephthalate, acrylic derivatives, such as polymethacrylates, polyglycolic—polylactic acid, polyvinylalcohol, gelatin, collagen and polyethyleneglycol. Examples of suitable lipid materials include waxes such as beeswax and lanolin, stearic acid and derivatives such as glycerol esters, fixed oils, fats, phospholipids, and glycolipids.

Such coatings are well known to persons skilled in this art. Persons skilled in the art could also readily provide coatings having a particular dissolution time so as to ensure that drug release is prevented until required.

The continuous phase used for forming the suspension of the pharmaceutically active substance is preferably water. The water may be admixed, if desired, with a co-solvent such as an alcohol, e.g. ethanol.

The free-flowing fluid suspension generally has a solids content of 50% by weight or less, more usually 5–25% by weight. A solids content of higher than 50% by weight results in the mixture becoming more akin to a paste rather than a fluid suspension.

Dosing from a fluid suspension rather than a paste offers advantages by facilitating the dosing and freeze-drying processes and producing product with a very rapid disintegration time. If dosed from a paste the disintegration time is generally much greater due to the overall higher content of solids.

According to the process of the invention, sedimentation in the drug suspension in the carrier material is controlled by manipulation of the matrix temperature to create a more viscous solution. By cooling a 3% gelatin solution from about 25° C. to about 15° C., the viscosity increases from about 2.0 mPa.s to 50.0 mPa.s. By following this approach, it is possible to sufficiently delay the rate of sedimentation of coated particles without significantly altering the physical properties of the finished units.

Other methods exist that could be used to increase the viscosity of the mix to prevent sedimentation such as the inclusion of polymers or viscosity modifying agents. Due to the nature of the dosage form however, the use of these compounds will tend to alter the finished properties of the units if included at a sufficient level to prevent sedimentation of the coarse particles. Such viscosity modifying agents include cellulose or cellulose derivatives such as ethylcellulose, hydroxyethylcellulose, hydroxypropylcellulose, caboxymethylcellulose, sodium hydroxypropylmethylcellulose, carbomer, xanthan gum, maltodextrin, acacia, tragacanth, povidone and polyvinyl alcohol. The presence of these polymers at the levels required to increase the viscosity causes an increase in the disintegration times of the dried units. When taken, the units disperse to form a gummy mass rather than the melting sensation obtained with ideal freeze-dried dosage forms.

It is also possible to adjust the density of the coated drug particles by selection of suitable lipids/polymers or combinations thereof and manipulation of the coat/drug ratio. By applying a sufficient coat to the drug particle of a lipid or waxy material that has a density lower than that of the drug particle or of the solution, the rate of sedimentation of the coated particle can be decreased.

In accordance with another aspect of the invention, an agent may be added to the suspension which gives increased structural integrity to the matrix. The structure-forming agent is typically a polyhydric alcohol, for example mannitol or sorbitol. The structure-forming agent is normally added to the suspension in an amount of about 1–5% by weight, for example about 2–4% by weight.

The suspension may also contain other additional ingredients such as, for example, flavoring agents and sweetening agents. Preservatives and coloring agents may also be added, The discrete units into which the suspension is formed may be liquid units, for example contained within the pockets of a suitable mold. Alternatively, the suspension may be in the form of solid units, for example frozen units or gelled units where the carrier material readily forms a gel. Typically each unit will contain up to 250 mg of the drug, for example 10–100 mg. Unit dosage forms of the drug in rapidly disintegrating form are encompassed by the present invention.

The suspension of the particles in the carrier material is preferably formed into discrete units by introduction into a mold which preferably comprises a plurality of depressions, each of the depressions being of the desired shape and size for the oral dosage form product. The mold preferably comprises a plurality of depressions formed in sheet of a filmic material which may be similar to the material employed conventionally in the blister packaging of pharmaceuticals. A preferred filmic material for use as a mold in the present invention is described in WO94/12142. The desired quantities of the suspension may be filled into the mold using an automatic filling means which delivers a predetermined dose into each of the depressions in the mold.

A covering material may be adhered to the film material in the areas surrounding the depressions after removal of solvent from the suspension filling the depressions. The covering sheet is preferably an aluminum foil or aluminum foil laminate which may be adhered to the film material around the depressions by, for example, a heat sensitive material. The cover sheet may be adhered to the film material in a manner such that it can peeled away by the user to uncover the oral dosage form in the depressions in the mold. Alternatively, it may be adapted to the oral dosage forms being pushed through.

Alternative methods of forming discrete frozen or gelled units of the suspension include solidifying the mixtures in dropwise fashion. For example, the suspension may be passed through one or more holes to form drops, spheres or a spray of small particles which can be solidified by passage through a cold gas or liquid, for example liquid nitrogen. Alternatively, the drops, spheres or spray may be solidified by contact with a chilled liquid which is immiscible with the solution or suspension and which has a density such that the drops either fall through the immiscible liquid as they solidify or float on the surface of the immiscible liquid.

Removal of the continuous phase from the discrete units of the suspension comprising the pharmaceutically active substance is carried out by techniques well known to those skilled in the art. For example, when the discrete units are in a liquid form, they will generally be frozen or gelled prior to drying. The suspension contained within the pockets of a suitable mold is frozen, for example by passing a gaseous cooling medium such as liquid nitrogen over the mold or by inserting the mold into a nitrogen spray freezing chamber. Alternatively, the mold may be cooled by passing the mold over a cold surface. Once the dosage forms have been frozen, the mold may be stored in a cold store prior to drying.

Frozen discrete units may be dried by freeze drying according to techniques which are well known in the art. The continuous phase, for example water, is sublimed in a freeze drying process under a reduced pressure which transforms the solid phase solvent (ice) directly into a vapor. The freeze drying process will generally be carried out in a freeze drying chamber typically operating under a vacuum of 0.1 to 1.0 mBar for a period of time of from 180 to 500 minutes.

Alternatively, frozen discrete units may be dried by a process as described in U.S. Pat. Nos. 5,120,549 and 5,330,763. According to that process, the pharmaceutically active substance and carrier material dispersed in a solvent is solidified and the solidified matrix is subsequently contacted with a second solvent that is substantially miscible with the first at a temperature lower than the solidification point of the first solvent. The matrix component is substantially insoluble in the second solvent and the first solvent is thereby removed from the matrix.

An alternative process for drying frozen discrete units is described in WO94/14422. In this process, the solvent is removed under conditions whereby the solvent is evaporated from the solid through the liquid phase to a gas, rather than subliming from a solid to a gas as in lyophilization. This is achieved by a vacuum drying at a temperature below the equilibrium freezing point of the composition at which point the solvent (such as water) changes phase.

When the discrete units are gelled units, any drying methods may be used which do not affect the properties of the preparations. For example, drying may be carried out at decreased pressure, or by forced-air drying. Drying at decreased pressure is preferable, and is typically carried out at a temperature of from 25° C. to 35° C. under a vacuum of −750 mmHg or less, for 2 to 5 hours. Drying using forced-air is preferably carried out at a temperature from 3° to 15° C. for 1 to 6 days.

The process of the invention is advantageously used to prepare oral solid rapidly disintegrating dosage forms of various pharmaceutically active substances. The invention is particularly adapted to the formation of oral solid rapidly disintegrating dosage forms of drugs having an unacceptable taste. For example, paracetamol, which is routinely incorporated into conventional tablets has a bitter taste, can be formulated according to the present invention into an oral rapidly disintegrating dosage form which does not have an unacceptable taste. By coating paracetamol with a polymer or lipid material to provide coated microparticles of paracetamol, and incorporating the microparticles into a matrix solution of gelatin and mannitol, it is possible to provide a rapidly disintegrating solid oral dosage form which does not rely on the use of sweeteners and flavoring agents (although such agents may optionally be present) to mask the taste of the drug.

Other classes of therapeutic agents which may be used are antacids, analgesics, anti-anginals, anti-anniety, anti-arrhythmics, anti-bacterials, anti-diarrhoeals, anti-depressants, anti-epileptics, anti-fungals, anti-histamines, anti-hypertensives, anti-inflammatory agents, anti-virals, cardiac agents, contraceptives, cough suppressants, cytotoxics, decongestants, diuretics, drugs for genito-urinary disorders, drugs for use in parkinsonism and related disorders, drugs for use in rheumatic disorders, hypnotics, minerals and vitamins, lipid lowering drugs and sex hormones. Veterinary drugs may also be processed according to the present invention.

EXAMPLES

The present invention will now be described in more detail with reference to the following non-limiting examples.

Example 1

| Material | % |
| --- | --- |
| Purified water | 85.10 |
| Gelatin | 2.80 |
| Mannitol | 2.10 |
| Ibuprofen | 10.00 |
| FDC Blue No. 2 | 0.0025 |

The gelatin and mannitol were added to the water and heated to 40° C. to dissolve before allowing to cool to 23° C. The mix was gradually added to the Ibuprofen powder (120 µm mean particle size) with manual mixing until a fluid suspension was formed. The remainder of the solution was then added.

Stirring was maintained in a thermostated water bath at 23° C. A 20 ml sample was transferred to a 20 ml glass vial and allowed to stand. The height of the sediment was measured at intervals and expressed as a percentage of the total suspension height. The presence of the blue dye facilitated this by enabling accurate determination of the sediment level. A sample was also taken and the viscosity measured using a Haake VT550 viscometer with an NV sensor. Viscosity values obtained are quoted at a shear rate of 500 s$^{-1}$. 0.5 ml aliquots (50 mg Ibuprofen) of the suspension were also dosed manually using a Gilson pipetteman into preformed PVC/PVdC blisters which were then frozen rapidly at −80° C. Freeze drying was then performed using a standard cycle. The blisters were then sealed with foil. Tensile strength measurements were performed to give a measure of relative unit physical strength, and disintegration tests were performed using the USP method.

The temperature of the mix was then adjusted, and after allowing to equilibrate for 45 minutes the measurements and dosing was repeated.

| Temperature (° C.) | Viscosity (mPa · s) | % sedimentation in 5 mines | Tensile strength Nmm$^{-2}$ | Disintegration time(s) |
|---|---|---|---|---|
| 25.0 | 3.34 | 7.3 | 0.22 | <2 |
| 23.0 | 4.22 | 6.7 | 0.22 | <2 |
| 20.5 | 5.09 | 5.3 | 0.25 | <2 |
| 18.2 | 12.3 | 2.7 | 0.27 | 3.8 |
| 15.8 | 38.5 | 0 | 0.37 | 2.0 |

The results demonstrate the increase in viscosity of the suspension as the temperature is decreased is sufficient to prevent any sedimentation of drug particles in a 5 minute period. Dosing of the suspension at 20° to 25° C. would have resulted in units containing different amounts of drug due to the rapid sedimentation. The tensile strength of the units also increases, but the disintegration times remain rapid throughout.

Example 2

| Material | % |
|---|---|
| Purified water | 74.99 |
| Gelatin | 3.00 |
| Mannitol | 2.50 |
| Coated paracetamol | 19.51 |
| FDC Blue No. 2 | 0.0025 |

The gelatin and mannitol were added to the water and heated to 40° C. to dissolve before allowing to cool to 23° C. The mix was gradually added to the coated paracetamol (200 μm particles, 82% potency, coated with a water insoluble polymer) with manual mixing until a fluid suspension was formed. The process was the same as in Example 1. Viscosity values obtained are quoted at a shear rate of 500 s$^{-1}$. 0.5 ml aliquots (80mg paracetamol) of the suspension were also dosed manually using a Gilson pipetteman into preformed PVC/PVdC blisters which were then frozen rapidly at −80° C. Freeze drying was then performed using a standard cycle. The blisters were then sealed with foil.

The temperature of the mix was then adjusted, and after allowing to equilibrate for 45 minutes the measurements and dosing was repeated.

| Temperature (° C.) | Viscosity (mPa · s) | % sedimentation in 5 mines | Tensile strength Nmm$^{-2}$ | Disintegration time(s) |
|---|---|---|---|---|
| 23.0 | 36.04 | 33 | 0.536 | 1.4 |
| 21.0 | 42.66 | 8.9 | 0.561 | 1.4 |
| 18.7 | 53.08 | 0 | 0.553 | 3.4 |
| 17.6 | 51.01 | 0 | 0.598 | 3.7 |
| 14.9 | 73.06 | 0 | 0.630 | 3.5 |

The results demonstrate the increase in viscosity of the suspension as the temperature is decreased. The disintegration times of the units do increase very slightly but are still rapid at viscosity levels sufficient to prevent any sedimentation in 5 minutes. When tasted, the units dispersed in the mouth with no bitter taste.

Example 3

| Material | % |
|---|---|
| Purified water | q.s. 100% |
| Gelatin | 3.00 |
| Mannitol | 2.50 |
| Coated paracetamol | 19.51 |
| Xanthan gum | 0–0.175 |
| FDC Blue No. 2 | 0.0025 |

Three batches were produced containing different levels of xanthan gum. The xanthan gum was dry blended with the mannitol before adding to the gelatin/water, but otherwise the process was the same as for Example 1. Viscosity and sedimentation measurements were added as well as dosing units.

| Xantham gum (%) | Viscosity (mPa · s) | % sedimentation in 5 minutes | Tensile strength Nmm$^{-2}$ | Disintegration time(s) |
|---|---|---|---|---|
| 0 | 36.04 | 33 | 0.536 | 1.4 |
| 0.05 | 36.4 | 6.3 | 0.319 | 1.4 |
| 0.125 | 50.2 | 0 | 0.512 | 12.1 |
| 0.175 | 64.2 | 0 | 0.605 | 20.1 |

At levels necessary to prevent sedimentation in 5 minutes, the disintegration times start to significantly increase. The units also dispersed forming a gummy mass.

Example 4

| Material | % |
|---|---|
| Purified water | q.s. 100% |
| Gelatin | 3.00 |
| Mannitol | 2.50 |
| Coated paracetamol | 19.51 |
| Carboxymethylcellulose sodium | 0–0.5 |
| FDC Blue No. 2 | 0.0025 |

Three batches were produced containing different levels of CMC Na. The CMC Na was added with vigorous stirng to the gelatin/mannitol/water solution, but otherwise the process was the same as for Example 1. Viscosity and sedimentations were made as well as dosing units.

| CMC Na (%) | Viscosity (mPa · s) | % sedimentation in 5 minutes | Tensile strength Nmm$^{-2}$ | Disintegration time(s) |
|---|---|---|---|---|
| 0 | 36.04 | 33 | 0.536 | 1.4 |
| 0.1 | 48.3 | 26 | 0.548 | 10.5 |
| 0.25 | 78.9 | 0 | 0.332 | 30 |
| 0.50 | 137 | 0 | 0.303 | 30 |

As with xanthan gum, the presence of CMC sodium at levels necessary to prevent sedimentation causes a significant increase in the disintegration times of the dried units. When taken, the units also formed a gummy mass.

Example 5

| Material | % |
| --- | --- |
| Purified water | q.s. 100% |
| Gelatin | 3.00 |
| Mannitol | 2.50 |
| Coated paracetamol | 19.51 |
| Carbopol 934P | 0–0.225 |
| Sodium hydroxide | q.s. pH 7 |
| FDC Blue No. 2 | 0.0025 |

Three batches were produced containing different levels of Carbopol 934P. The Carbopol 934P was dry blended with the mannitol before adding to the gelatin/water, but otherwise the process was the same as for Example 1. Viscosity and sedimentation measurements were made as well as dosing units.

| Carbopol 984P (%) | Viscosity (mPa · s) | % sedimentation in 5 minutes | Tensile strength Nmm$^{-2}$ | Disintegration time(s) |
| --- | --- | --- | --- | --- |
| 0 | 36.04 | 33 | 0.536 | 1.4 |
| 0.05 | 35.8 | 15 | 0.238 | 7.0 |
| 0.10 | 77.3 | 6 | 0.227 | 20.2 |
| 0.20 | 156 | 0 | 0.329 | >30 |
| 0.225 | >150 | 0 | 0.310 | >30 |

As with xanthan gum and CMC sodium, the presence of Carbopol 934P at levels necessary to prevent sedimentation causes a significant increase in the disintegration of the dried units. When taken, the units also formed a gummy mass.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A process for preparing an oral solid rapidly disintegrating dosage form of a pharmaceutically active substance, comprising the steps of:

forming a suspension in a continuous phase of coarse particles of a pharmaceutically active substance in a carrier material, said carrier material being selected from the group consisting of water-soluble and water-dispersible carrier materials;

reducing the temperature of the suspension to form a cooled suspension of increased viscosity;

forming discrete units of said cooled suspension; and removing the continuous phase to leave said rapidly disintegrating form in said carrier material.

2. A process according to claim 1, wherein said continuous phase comprises water.

3. A process according to claim 1, wherein said carrier material is gelatin.

4. A process according to claim 1, wherein said coarse particles are uncoated or coated with a coating which delays release of the pharmaceutically active substance beyond the point of disintegration of said form on the tongue.

5. A process according to claim 4, wherein said coating is selected from a group consisting of a polymeric material and a lipid material.

6. A process according to claim 5, wherein said polymeric material is selected from the group consisting of cellulose, a cellulose derivative, an acrylic derivative, polyglycolic—polylactic acid, polyvinylalcohol, gelatin, collagen and polyethyleneglycol.

7. A process according to claim 6, wherein said cellulose derivative is selected from the group consisting of ethylcellulose, hydroxyethylcellulose, hydroxypropylmethylcellulose, hydroxypropylcellulose, methylcellulose, cellulose acetate, cellulose acetate phthalate and hydroxypropylmethylcellulosephthalate, and said acrylic derivative is a polymethacrylate.

8. A process according to claim 5, wherein said lipid material is selected from the group consisting of a wax, lanolin, stearic acid, a stearic acid derivative, a phospholipid and a glycolipid.

9. A process according to claim 8, wherein said stearic acid derivative is selected from the group consisting of a glycerol ester, a fixed oil and a fat.

10. A process according to claim 1, wherein said coarse particles have a size in the range of 50 µm to 400 µm.

11. A process according to claim 1, wherein a structure-forming agent is added to the suspension.

12. A process according to claim 11, wherein said structure-forming agent is selected from the group consisting of mannitol and sorbitol.

13. A process according to claim 11, wherein said structure-forming agent is added in an amount of 1 to 5% by weight.

14. A process according to claim 1, wherein the temperature of the suspension is reduced such that the viscosity is increased to a level sufficient to prevent sedimentation of the drug over a period of 5 minutes.

15. A process according to claim 1, wherein the temperature of the suspension is reduced to about 15–19° C.

16. A process according to claim 1, wherein said continuous phase is removed by freeze drying.

17. A process according to claim 1, wherein said coarse coated particles contain about 10 to 95% by weight of pharmaceutical substance.

18. A process according to claim 1, wherein said dosage form disintegrates in water in less than 10 seconds.

19. A process according to claim 1, wherein said suspension has a solids content in the range of less than 50% by weight.

20. An oral solid rapidly disintegrating dosage form of a pharmaceutically active substance when prepared by a process according to claim 1.

21. A process according to claim 1, wherein said cooled suspension is formed into discrete units by introduction into a mold.

22. A process according to claim 21, wherein said mold comprises a plurality of depressions each of a shape and size for said oral dosage form.

23. A process according to claim 21, wherein said cooled suspension in said mold is frozen.

* * * * *